(12) United States Patent
Monnier et al.

(10) Patent No.: US 11,396,491 B2
(45) Date of Patent: Jul. 26, 2022

(54) MONOFUNCTIONAL OR MULTIFUNCTIONAL URETHANE ACRYLATE OLIGOMERS WITHOUT ISOCYANATES

(71) Applicant: Arkema France, Colombes (FR)

(72) Inventors: Guillaume P. Monnier, Avrigny (FR); Catherine M. Leroy, Lille (FR)

(73) Assignee: Arkema France, Colombes (FR)

( * ) Notice: Subject to any disclaimer, the term of this patent is extended or adjusted under 35 U.S.C. 154(b) by 46 days.

(21) Appl. No.: 15/519,365

(22) PCT Filed: Oct. 13, 2015

(86) PCT No.: PCT/FR2015/052754
§ 371 (c)(1),
(2) Date: Aug. 17, 2017

(87) PCT Pub. No.: WO2016/059340
PCT Pub. Date: Apr. 21, 2016

(65) Prior Publication Data
US 2017/0342024 A1  Nov. 30, 2017

(30) Foreign Application Priority Data

Oct. 15, 2014  (FR) ...................................... 1459890

(51) Int. Cl.
| | | |
|---|---|---|
| *C08G 71/04* | (2006.01) | |
| *C09D 175/16* | (2006.01) | |
| *C09D 4/00* | (2006.01) | |
| *C07C 271/12* | (2006.01) | |
| *C09J 175/16* | (2006.01) | |
| *C08F 22/22* | (2006.01) | |

(52) U.S. Cl.
CPC ............ *C07C 271/12* (2013.01); *C08F 22/22* (2013.01); *C08G 71/04* (2013.01); *C09D 4/00* (2013.01); *C09D 175/16* (2013.01); *C09J 175/16* (2013.01); *C08G 2190/00* (2013.01)

(58) Field of Classification Search
None
See application file for complete search history.

(56) References Cited

U.S. PATENT DOCUMENTS

| 4,544,725 A | 10/1985 | Priola et al. |
| 4,758,632 A * | 7/1988 | Parekh ................. C07C 271/20 525/383 |
| 2004/0192803 A1 | 9/2004 | Figovsky et al. |
| 2004/0254292 A1 | 12/2004 | Williams |
| 2013/0004677 A1 | 1/2013 | Hwang et al. |

FOREIGN PATENT DOCUMENTS

CN  103483905  *  1/2014

* cited by examiner

*Primary Examiner* — Ana Z Muresan
(74) *Attorney, Agent, or Firm* — Christopher R. Lewis

(57) ABSTRACT

An acrylated and/or methacrylated urethane oligomer obtained by reaction of a specific polyamine with a cyclic carbonate compound carrying m cyclic carbonate groups, giving an intermediate product carrying m formed urethane groups which carry residual reactive amine —NH— groups, and subsequently an addition reaction of each of the residual reactive amine groups of the intermediate product with an acrylate group of a compound carrying, in addition to the acrylate group, p additional acrylate and/or methacrylate groups, with each residual reactive amine —NH— group of the intermediate product being thus converted into a carbon-nitrogen bond carrying the acrylate and/or methacrylate groups, and thus production of the urethane oligomer, with the urethane oligomer carrying m urethane groups and m hydroxyl groups and having a functionality in acrylates and/or methacrylates ranging from $m*p(n-1)$ to $m*p(2n-2)$.

12 Claims, No Drawings

MONOFUNCTIONAL OR MULTIFUNCTIONAL URETHANE ACRYLATE OLIGOMERS WITHOUT ISOCYANATES

CROSS-REFERENCE TO RELATED APPLICATIONS

This application is a U.S. national stage application under 35 U.S.C. § 371 of PCT/FR2015/052754, filed Oct. 13, 2015, which claims benefit to French patent application number 1459890, filed Oct. 15, 2014.

FIELD OF THE INVENTION

The invention relates to novel urethane oligomers which are monofunctional or multifunctional in acrylate and/or methacrylate groups, with the urethane group being obtained without any use of isocyanate, by a carbonate-amine reaction favourable to the environment and to health. The invention uses an NIPU (Non-Isocyanate Polyurethane) route. It makes possible the selective production of acrylate and/or methacrylate groups with a minimum functionality of 1 but which can be high and with, in addition to this functionality, one hydroxyl functionality per urethane bond created. These oligomers can be used as crosslinkable binders for compositions for coatings, for adhesives, for moulding or for leaktightness agents, for chemical sealing, for systems for the layer-by-layer manufacture of 3D objects, for 3D printing systems or for concrete or for composite.

BACKGROUND OF THE INVENTION

The current synthesis of (meth)acrylate methane oligomers resorts to the use of isocyanate compounds or polyisocyanate compounds for the multifunctional oligomers. These compounds are toxic and the handling and use thereof require particular and strict precautions in order to protect human health and for the environment in general. Furthermore, the urethanization reaction (formation of urethane bond by reacting an alcohol with an isocyanate) commonly uses tin-based catalysts, which compounds are also toxic and harmful to the environment.

SUMMARY OF THE INVENTION

Recent years have seen an important development in the carbonate-amine reaction as alternative route for the formation of a urethane bond without use of isocyanates. This is because this reaction makes it possible to access hydroxylated urethane compounds without the release of secondary compounds when it involves a cyclic carbonate, that is to say a carbonate ring having 5 or 6 atoms, with hydroxyls in the respective beta and gamma positions with respect to the urethane group. "Non-Isocyanate Polyurethane" (abbreviated to NIPU) compounds are then obtained. The carbonates are regarded as not very toxic or dangerous in general. Moreover, it is possible to prepare these carbonates by addition of $CO_2$ to an epoxy functional group of an epoxide compound. The preparation of the said carbonates by such a route thus consumes $CO_2$, which is a greenhouse gas. Thus, subject to the adoption of this method of preparation, the replacement of the alcohol-isocyanate reaction by the carbonate-amine reaction is beneficial both with regard to safety and to the environment in general.

DETAILED DESCRIPTION OF THE INVENTION

The objective of the present invention is novel acrylate or methacrylate urethane oligomers with a structure which is well controlled and reproducible in terms of chain length and of functionality, in particular without crosslinked structure, when a polyamine carrying from 2 to 5 primary and/or secondary amine groups is reacted with a carbonate compound which can carry up to two cyclic carbonate functional groups. These oligomers can be monofunctional, both in acrylates and in methacrylates, and/or in particular oligomers which are multifunctional in acrylates and/or methacrylates, and more particularly with a functionality of at least 3, which are suitable for crosslinking by the UV radical route or by the peroxide route or by a dual route, the dual route being a mixed route using a peroxide by the thermal route and a photoinitiator by the UV route.

The present invention makes it possible in particular to access such acrylate or methacrylate urethane oligomers without specific restriction in the handling or the storage of the starting materials used, which are nontoxic and friendly to the human health and the environment in general and commercially available.

The present invention more particularly relates to oligomers carrying aminoacrylate urethane groups and, as final reactive groups, acrylates and/or methacrylates and hydroxyls in the beta or gamma position with respect to the said urethane bond as a function of the number of atoms of the carbonate ring of 5 or 6 atoms respectively. The urethane and hydroxyl groups generated are in number different from (lower) and in positioning of the urethane bond independent of the acrylate or methacrylate groups without a direct urethane-acrylate or methacrylate ester bond. There is thus a multiplying effect on the final functionality of the oligomer of the invention in acrylate and/or methacrylate groups, with control of the structure and of the functionality of the said oligomers and without risk of formation of gels during their preparation, in particular when oligomers which are multifunctional in acrylates and/or methacrylates are targeted. These oligomers exhibit in particular a very satisfactory rate of crosslinking under UV radiation and make it possible to obtain crosslinked finished applicational products, in particular coatings, having a good flexibility and a hardness which can be adjusted as a function of the choice of the reactants. Thus, the coatings obtained exhibit in particular a good compromise in performance between hardness and flexibility while having the advantages of the presence of the urethane and aminoacrylate groups in addition. These advantages are in particular: chemical resistance, resistance to solvents, abrasion and wear resistance and synergistic acting effect on the aminoacrylate bonds during the photocrosslinking.

The other specific advantage of the invention is that it makes it possible to obtain multiacrylate and/or multimethacrylate polyurethane oligomers by a simpler process and in only two stages, in comparison with the multiple stages often necessary in the normal processes for obtaining acrylated and/or methacrylated urethane oligomers.

The first subject-matter of the invention is a urethane oligomer which is monofunctional or multifunctional in acrylates and/or methacrylates, obtained from the reaction of a specific polyamine a) with a cyclic carbonate compound b), the said polyamine being in stochiometric excess and giving an intermediate product c) carrying residual reactive amine groups, and, in a second stage, the addition of each of the said residual reactive amine —NH— groups to an acrylate group of a compound d) carrying, in addition to the said acrylate group, additional acrylate or methacrylate groups, with production of the said urethane oligomer according to the invention.

The present invention also relates to a process for the preparation of the said oligomer comprising two stages: i) reaction of the said polyamine a) with the said carbonate b), giving the said intermediate product c), and ii) reaction for the modification of the said product c) by a Michael addition reaction of each of the said residual reactive amine —NH— groups with an acrylate group of the said compound d).

Another subject-matter of the invention is a crosslinkable composition comprising at least one oligomer as defined according to the present invention.

The present invention also covers the use of the said oligomer as reactive binder in coating compositions, including paints, varnishes, inks, adhesive compositions, moulding compositions, leaktightness agent compositions, chemical sealing compositions, compositions for systems for the layer-by-layer manufacture of 3D objects, compositions for 3D printing systems, concrete compositions or composite compositions.

Finally, the present invention covers the finished product which results from the use of at least one oligomer as defined in the present invention or an oligomer as obtained by the process of the invention, this finished product preferably being chosen from: coatings, including paints, varnishes and inks, adhesives, moulded parts, 3D objects obtained layer-by-layer, 3D printing objects, leaktight seals, chemical sealing, finished concrete or composite articles.

The first subject-matter of the invention is thus a urethane oligomer which is monofunctional or multifunctional in acrylates and/or methacrylates, preferably acrylates, which can be obtained from the reaction of a specific polyamine a) with a cyclic carbonate compound b) carrying m cyclic carbonate groups, the said polyamine being in stochiometric excess with respect to b) and the said reaction giving an intermediate product c) carrying m formed urethane groups, which groups carry residual reactive amine —NH— groups, and subsequently by an addition reaction of each of the said residual reactive amine groups of the said product c) with an acrylate group of a compound d) carrying, in addition to the said acrylate group, p additional acrylate and/or methacrylate groups, with each residual reactive amine —NH— group of the said product c) being thus converted into a carbon-nitrogen bond carrying the said acrylate and/or methacrylate groups, and thus production of the said urethane oligomer, with the said polyamine a) carrying n primary and/or secondary amine groups and optionally at least one tertiary amine group, with n ranging from 2 to 5, preferably from 2 to 4 and more preferably from 2 to 3, more preferably still of 2, the said carbonate b) carrying m cyclic carbonate groups with m ranging from 1 to 2, the ring of the said cyclic carbonate groups preferably being a ring having 5 or 6 atoms, the said intermediate product c) carrying m urethane groups and m OH groups in the alpha or beta position with respect to the said urethane group and c) carrying from m*(n−1) to m*(2n−2) residual reactive amine —NH— groups, the said compound d) carrying p acrylate and/or methacrylate groups in addition to the said acrylate group which reacts with one of the said residual reactive amine —NH— groups, with p being at least equal to 1 and preferably at least equal to 2, and the number of the said residual reactive amine —NH— groups of the said product c) being less than or equal to the number of moles of the said compound d), each carbon-nitrogen bond formed carrying p acrylate and/or methacrylate groups and the said urethane oligomer carrying m urethane groups and m hydroxyl groups in the alpha or beta position with respect to the said urethane and having a functionality in acrylates and/or methacrylates ranging from m*p(n−1) to m*p (2n−2).

The said n primary and/or secondary amine groups of the said polyamine a) can be carried by a radical A of valency n, which radical A can be or comprise an aliphatic, cycloaliphatic or aromatic structure with, in the latter case, the said n amine groups being carried by at least one alkylene group attached to the aromatic nucleus, and the rings of the said m cyclic carbonate groups of the said carbonate b) have 5 or 6 atoms and are carried by a radical $R_3$ of valency m, with $R_3$ being a hydrocarbon radical of aliphatic, cycloaliphatic or aromatic structure and optionally hydroxylated or $R_3$ can be a simple hydrogen when m=1; optionally, the carbonate ring can be substituted by an optionally hydroxylated hydrocarbon substituent $R_4$, it being possible for $R_4$ to be of aliphatic, cycloaliphatic or aromatic structure identical to or different from that of $R_3$ and it optionally being possible for $R_4$ to form a ring attached to the carbonate ring by two common carbon atoms.

The term "reactive" relating to the said residual reactive amine —NH— groups means, according to the present invention, "which can react by a Michael addition with an acrylate functional group with formation of an aminoacrylate —N—$CH_2$—$CH_2$—$CO_2$— group".

On the basis of the said radical A, the said polyamine a) can be represented overall by: $(R'_1—NH—)_x A(-NH_2)_y$, with $R'_1$ being an alkyl or cycloalkyl or aralkyl and with x+y=n.

The cycloaliphatic structure as mentioned above comprises polycyclic structures, such as aliphatic bicycles or tricycles.

More particularly, the said polyamine a) can be of aliphatic $C_2$ to $C_{54}$ structure or of cycloaliphatic structure, including polycyclic structure, such as bicycle or tricycle, or it can comprise an aromatic structure with the amine functional groups carried by alkylenes attached to the aromatic nucleus.

The said polyamine a) can be of monomeric structure and thus without a repeat unit or of oligomeric structure with at least two monomeric repeat units bonded to an amine group, for example alkyleneimine, as a repeat unit, in particular ethyleneimine, or to another group, such as an ether, ester or amide.

According to a specific option related to the structure of the radical A of the said polyamine a) carrying the said n primary and/or secondary amine groups, the said polyamine a) is chosen from:

a $C_2$ to $C_{54}$ alkylenepolyamine, the said alkylene being a linear or branched $C_2$ to $C_{54}$ alkylene and carrying the said n primary and/or secondary amine groups, a polyamine comprising at least two repeat units from: $C_2$ to $C_4$ alkyleneimine, in particular ethyleneimine or propyleneimine, preferably ethyleneimine, the said polyamine a) being in this case an oligoalkyleneimine-polyamine, in particular a polyethyleneiminepolyamine, including of dendritic structure, a polyamine comprising one or more units from: ether, ester-amide or amide, with, in the case of the presence of several units, the said polyamine a) being chosen from: oligoether polyamines, oligoester amidepolyamines or multiesteramidepolyamines.

Mention may be made, among $C_2$ to $C_{54}$ polyamines a), of diamines or triamines having a linear aliphatic chain from alkylenediamines or alkylenetriamines, including fatty $C_{36}$ diamines or fatty $C_{54}$ triamines, with it being possible for the said alkylenes to be alkoxylated or nonalkoxylated.

Among polyamines, one or more units from: ether, ester-amide or amide, mention may be made, in the case of several units, of polyethyleneiminepolyamines, preferably oligoethyleneiminepolyamines, oligoetherpolyamines, such as Jeffamines R, oligoester-amidepolyamines or multi(ester-amideamines) which are multifunctional esters terminated (each ester) by an amide-amine group.

As regards the said overall functionality f of the said urethane oligomer according to the invention, it can have the minimum value when all the amine groups of the polyamine a) are all secondary and the maximum value when all the amine groups of the polyamine a) are primary. Consequently, this functionality f can vary only between the two limits as defined.

According to a specific alternative form, the said polyamine a) is chosen from polyamines of following formulae a1) and a2):

a1) $R_1$—NH—$R_2$—(NH—R)(NH—R')$_{n1}$, with $n_1$ being equal to 3, 2, 1 or 0 and preferably $n_1$ being equal to 2, 1 or 0, a2) $R_1$—NH—(R'$_2$NH)$_{n2}$—R"$_2$—NH—R' with $n_2$ being equal to 3, 2 or 1, with $R_1$ and R and R' being independently chosen from: H, alkyl, preferably $C_1$-$C_3$ alkyl, the said alkyl optionally being alkoxylated or a cycloalkyl, with it being possible for $R_1$ to be identical to or different from R and R' and with it being possible for R and R' to be identical or different and in particular with R and/or R' being different from H, $R_2$ being alkylene or cycloalkylene (comprising an aliphatic $C_6$ ring) or aralkylene of valency n ranging from 2 to 5, with it being possible for $R_2$ to carry or comprise at least one tertiary amine group, and it being possible for R'$_2$ and R"$_2$ to be identical or different and to be chosen from alkylenes, preferably $C_2$ to $C_8$ alkylenes and more preferably $C_2$ to $C_6$ alkylenes, and, if R"$_2$ is different from R'$_2$, in this case it being possible for R"$_2$ to carry or comprise at least one tertiary amine group.

According to a specific embodiment of the said oligomer according to the invention, the said polyamine a) is an amine according to formula a2) as defined above, with $n_2$=1 and $R_1$ and R' being H and R'$_2$ and R'$_2$ being identical or different $C_2$ to $C_6$ alkylenes, in particular $C_2$ to $C_4$ alkylenes, the said amine a2) being more particularly selected from 3-[(2-aminoethyl)amino]propylamine or bis(3-aminopropyl) amine.

According to a specific choice, the said polyamine a) is an amine defined according to formula a2), as described above, with $n_2$=2 or 3 and $R_1$ and R' being H and R'$_2$ and R'$_2$ being identical $C_2$ to $C_4$ alkylenes, in particular $C_2$ to $C_3$ alkylenes, the said amine a2) being more particularly selected from triethylenetetramine or tetraethylenepentamine.

More particularly, the said polyamine is a diamine (n=2) and is preferably selected from secondary-primary diamines, more preferably from: N-methyl-1,3-propanediamine, N-methylethanediamine, N-methyl-1,4-butanediamine or N-methyl-1,5-pentanediamine.

According to a second particularly preferred option, the said polyamine a) is a diamine (n=2) and it is secondary-secondary, more preferably: N-methyl-N'-methyl-1,3-propanediamine, N-methyl-N'-methylethanediamine, N-methyl-N'-methyl-1,4-butanediamine or N-methyl-N'-methyl-1,5-pentanediamine.

The carbonate compound b) according to the invention can be represented overall by the overall formula $R_3$(-cyclocarbo)$_m$, with m ranging from 1 to 2 and "cyclocarbo" being the said cyclic carbonate group.

The said compound b) can be a mixture of carbonate compounds carrying m=1 and/or m=2 cyclic carbonates. When m is between 1 and 2, it is a mixture of at least one monocarbonate b) with m=1 and of at least one dicarbonate b) with m=2.

The polyamine a) can also be a mixture of different polyamines a) of different nature and/or with n different or identical.

The compounds d) can also be a mixture of at least two compounds d) according to the invention of different nature with a different or identical functionality.

The definition of the said hydrocarbon radical $R_3$ carrying m cyclic carbonate groups in the said cyclic carbonate compound b) depends on the structure of the said carbonate b). In particular, the said carbonate b) is a complete or partial ester of a monomeric or oligomeric polyacid, such as an oligoester polyacid, with a hydroxylated carbonate, preferably glycerol carbonate, or b) is a complete or partial ether of a monomeric or oligomeric polyol, such as oligoester or oligoether polyol, with a hydroxylated carbonate, preferably glycerol carbonate, or b) is a complete or partial ether of a phenolic derivative, including bisphenol A or dihydroxyphenylene, with a hydroxylated carbonate, preferably glycerol carbonate, or b) is an ether of allyl or vinyl alcohol with a hydroxylated carbonate, preferably glycerol carbonate or a methacrylate of a hydroxylated carbonate, preferably glycerol carbonate, or b) is a carbonate obtained by addition of $CO_2$ to a precursor monomeric or oligomeric epoxidized compound or b) is the product of the reaction of dimethyl carbonate with an aliphatic or cycloaliphatic polyol with a functionality of at least 2, preferably ranging from 2 to 6.

More particularly, the said epoxidized precursor can be an epoxidized oligodiene, a methyl or ethyl ester of an epoxidized unsaturated fatty acid or an epoxidized derivative of an unsaturated fatty alcohol (mono- or diunsaturated fatty chain) or an epoxidized prepolymer obtained by amine-epoxide reaction, polyester prepolymer epoxidized by anhydride-epoxy reaction, epoxidized acrylic oligomer and/or epoxidized styrene oligomer or an ether of glycidyl alcohol with a polyol or an ester of glycidyl alcohol with a polyacid, with it being possible for the said polyol or polyacid to be monomeric or oligomeric, or an epoxidized olefin (for m=1) or an epoxidized diolefin.

Thus, when the said epoxidized precursor is an epoxidized oligodiene or an epoxidized unsaturated fatty acid ester or an epoxidized unsaturated fatty alcohol derivative, in this case the said carbonate b) can be an aliphatic chain which is mono- or multifunctional in cyclic carbonates with 2 carbon atoms of the carbonate ring of the said carbonate compound b) forming an integral part of the said chain.

As already described, the said carbonate b) can also be obtained by the reaction of dimethyl carbonate with an aliphatic or cycloaliphatic polyol with a functionality of at least 2, preferably between 2 to 6.

According to a specific option, the said carbonate ring is substituted by the said substitution $R_4$ as defined above, which is an optionally alkylene hydroxylated alkyl, and in a more specific option $R_4$ can form a ring attached to the carbonate ring by 2 common carbon atoms.

According to a preferred alternative form of the invention, the ring of the cyclic carbonate b) is a ring having 5 atoms.

The carbonate compounds b) can also be obtained from a mono- or polyepoxidized precursor, preferably a polyepoxidized precursor, carrying m epoxy groups, modified to give cyclic carbonates by the addition of carbon dioxide to the said epoxy groups.

Mention may be made, as epoxidized oligodiene, of an epoxidized oligobutadiene or an epoxidized polyisoprene or oligomeric epoxidized copolymers of butadiene and isoprene. Mention may be made, as epoxidized diolefin or olefin, of epoxidized dicyclopentadiene, epoxidized norbornene, epoxidized cyclohexene or epoxidized cyclohexadiene, which are carbonates b) of cycloaliphatic structure. Mention may also be made, as precursor epoxidized compound of a carbonate suitable as cyclic carbonate b) according to the invention, of the epoxidized prepolymers obtained with an excess of epoxide by amine-epoxide reaction or polyester prepolymer epoxidized by anhydride-epoxy reaction, epoxidized acrylic and/or styrene oligomer, in particular acrylic and/or styrene copolymer of glycidyl methacrylate, or a polyepoxidized monomer which is a glycidyl ether or ester, in particular the glycidyl ether derivatives of bisphenols, which are preferably hydrogenated, or the glycidyl ethers of aliphatic polyols or cycloaliphatic polyols, or glycidyl esters of polyacids with an initial carboxyl functionality m before esterification.

Any epoxide of monomeric structure or of oligomeric structure which is linear or branched, with, in the case of oligomer, preferably having a number-average molecular weight Mn of less than 1000 and preferably of less than 600 daltons, measured by GPC in polystyrene equivalents, may be suitable as polyepoxidized precursor compound.

More particularly, the precursor epoxidized compound of the said carbonate b) according to the invention can be a diepoxide monomer and can be chosen from: ethylene glycol diglycidyl ether, propylene glycol diglycidyl ether, butanediol diglycidyl ether, neopentyl glycol diglycidyl ether, hexanediol diglycidyl ether, cyclohexanedimethanol diglycidyl ether, hydrogenated or nonhydrogenated bisphenol A diglycidyl ether (BADGE) or hydrogenated or nonhydrogenated bisphenol F diglycidyl ether (BFDGE), these compounds optionally being alkoxylated, for example with 1 to 4 alkoxy units, such as ethoxy and/or propoxy, or diglycidyl ester of ortho-, iso- or terephthalic acid, diglycidyl ester of tetrahydrophthalic acid or diglycidyl ester of hexahydrophthalic acid.

The said mono- or polyepoxidized compound, in particular diepoxidized compound, can also be an epoxidized oligomer or an epoxidized resin, such as epoxidized oils, in particular soybean oil, epoxidized polybutadiene or a condensation or addition prepolymer carrying epoxide (or epoxy or oxirane) end groups. The epoxy functionality of this epoxidized compound should correspond to the functionality m in cyclic carbonates of the said targeted carbonate b). For example, for a dicarbonate, that is to say having 2 cyclic carbonates, the epoxidized precursor is preferably a diepoxide, also known as diepoxy.

The said carbonate b) for m=2 can also alternatively be the product of the reaction of dimethyl carbonate with an aliphatic or cycloaliphatic polyol with a functionality of at least 2, preferably ranging from 2 to 6, with formation of the said cyclic carbonate compounds b) as defined according to the invention.

The said compound d) is a multifunctional acrylate, in so far as it carries at least one acrylate group, one acrylate being the minimum if the other group is a methacrylate, and at least two acrylates in the absence of any methacrylate group with a minimum of two acrylates in this case. This minimum of starting functionality of the said compound d) is that required when the targeted product is a urethane oligomer which is monofunctional in acrylate or methacrylate starting from a monofunctional carbonate compound b) and a bifunctional polyamine a) (n=2).

It should be noted that the reaction between an amine group, whether it is primary or secondary, and a carbonate group always gives a urethane group, with the only difference, in the case of a secondary amine group in comparison with the primary amine, that the nitrogen atom of the urethane group is substituted (if secondary amine) instead of carrying a hydrogen (if primary amine).

On the other hand, the two residual —NH— groups of a primary amine group after the formation of the m urethane groups can react with two acrylate groups on two different molecules of compound d).

The said compound d) can be represented overall by

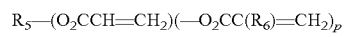

with $R_5$ being a hydrocarbon residue of valency p+1 and $R_6$ being H or methyl for a portion or all of the p groups, and preferably $R_5$ is a polyol residue chosen from optionally alkoxylated and/or substituted alkylene polyol, optionally substituted cycloalkylene polyol or aralkylene polyol optionally alkoxylated and/or substituted on the aromatic ring or polyether polyol or polyester polyol or $R_5$ is a residue of a multifunctional epoxy acrylate compound carrying an acrylate group and p additional acrylate and/or methacrylate groups.

The said compound d) is, according to a first option, a multifunctional acrylic monomer having a functionality of at least 2, in particular greater than 2 and ranging up to p+1 equal to 6 and selected from:

d1) acrylate esters of alkoxylated or nonalkoxylated polyols, preferably polyols chosen from the group: trimethylolpropane, ditrimethylolpropane, pentaerythritol, dipentaerythritol, diethylene glycol, dipropylene glycol, tripropylene glycol, glycerol, propylene glycol, butanediol and hexanediol, or d2) epoxy acrylates, d3) aminoacrylates.

According to a second option, the said compound d) is a multifunctional acrylic oligomer having a functionality of at least 2, in particular greater than 2 and ranging up to p+1 equal to 12 and selected from:

d4) acrylated acrylic oligomer which can be an acrylated glycidyl methacrylate copolymer or acrylated styrene oligomer which can be a copolymer of styrene with maleic anhydride or acrylic acid which is acrylated by hydroxyethyl acrylate, d5) acrylated hydroxylated oligomer, in particular from acrylated hydroxylated polydienes, preferably acrylated hydroxylated polybutadiene and more preferably acrylated hydrogenated hydroxylated polybutadiene, d6) acrylated epoxidized oil, d7) acrylated epoxidized oligodiene, d8) oligoether acrylates, d9) oligoester acrylates, d10) oligoaminoacrylates.

The term "acrylates" according to these options below means that the compound d) can carry only acrylate —O$_2$C—CH═CH$_2$ groups or else it can carry at least one acrylate and p groups, a portion or all of which are methacrylate groups according to —O$_2$C—C(CH$_3$)═CH$_2$. According to a specific option, d) carries only acrylate groups (without methacrylate), which gives a greater reactivity to the corresponding oligomer according to the invention.

According to a particular preference of the said oligomer according to the invention, the said polyamine a) is a diamine. More specifically, the said polyamine a) can be a diamine selected from secondary-primary, primary-primary or secondary-secondary diamines, preferably secondary-primary or secondary-secondary diamines.

According to a more particular option, the said diamine is selected from secondary-primary diamines, preferably from: N-methyl-1,3-propanediamine, N-methylethanediamine, N-methyl-1,4-butanediamine or N-methyl-1,5-pentanediamine.

According to another more particular option, the said diamine is selected from secondary-secondary diamines, preferably from: N-methyl-N'-methyl-1,3-propanediamine, N-methyl-N'-methylethanediamine, N-methyl-N'-methyl-1,4-butanediamine or N-methyl-N'-methyl-1,5-pentanediamine.

According to a particularly preferred option of the oligomer of the invention, the carbonate ring of the said carbonate b) has 5 atoms, the said polyamine a) is a secondary-primary diamine with $n_1$=0 and R═H, as defined according to formula a1) as defined above, and the said oligomer comprises at least one oligomer of following general formula (I):

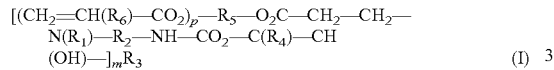

[(CH$_2$═CH(R$_6$)—CO$_2$)$_p$—R$_5$—O$_2$C—CH$_2$—CH$_2$—N(R$_1$)—R$_2$—NH—CO$_2$—C(R$_4$)—CH(OH)—]$_m$R$_3$      (I)

with
$R_1$ being as defined above in the formula a1),
$R_2$ being as defined above in the formula a1),
$R_3$ being as defined for the compound b), the radical of valency m carrying the said m cyclic carbonate groups,
$R_4$ being the said optional substituent of the carbonate ring as defined above,
$R_5$ being as defined for the said compound d) above,
$R_6$ being H or methyl or H and methyl if p is other than 1.

According to another option, the said carbonate ring of the said carbonate b) has 6 atoms, the said polyamine a) is a secondary-primary diamine with $n_1$=0 and R═H, as defined according to formula a1) above, and the said oligomer comprises at least one oligomer of following general formula (II):

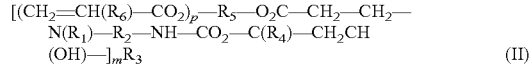

[(CH$_2$═CH(R$_6$)—CO$_2$)$_p$—R$_5$—O$_2$C—CH$_2$—CH$_2$—N(R$_1$)—R$_2$—NH—CO$_2$—C(R$_4$)—CH$_2$CH(OH)—]$_m$R$_3$      (II)

with $R_1$, $R_2$, $R_3$, $R_4$, $R_5$ and $R_6$ being as defined above in formula (I).

More particularly, the functionality f in acrylate and/or methacrylate groups of the said urethane oligomer according to the present invention can vary from 1 to 30, preferably from 2 to 20 and more particularly from 3 to 20.

According to a particular and preferred case of oligomer as defined according to the invention, p varies from 1 to 11, preferably from 2 to 11, more preferably from 2 to 5, more preferably still being greater than 2 and ranging up to 5.

According to a more particular case for this oligomer of the invention, m=2 and p varies from 2 to 11 and preferably p varies from 3 to 5.

The said oligomer is of linear or branched structure. By definition, it cannot comprise a crosslinked structure, which is thus excluded. A person skilled in the art knows in particular to choose the proportions and the functionalities of reactive components and also the degree of conversion of the reactive functional groups in order to prevent any chemical gelling or crosslinking of the reactive system. This question can only be posed when one of the reactive components a) or b) or a) and b) initially in the reaction of the first stage has a functionality greater than 2, that is to say when a branched structure is targeted. In this case, it is possible to control the structure without any possible crosslinking by adjusting the proportions of the reactants so that the number-average functionality (per mole of reactant component) over the whole of the reactive components (a)+b)) does not exceed 2 or, if it exceeds 2, to limit the degree of conversion well before the predictable gel (gelation) point, which point is predictable either by experimentation or by the calculation according to the Macosko-Miller relationship, and/or by gradual addition of the least functionalized component to the most functionalized component with efficient stirring (maintained in excess of reactive functional groups by the gradual addition of the second reactive component). The abovementioned Macosko-Miller relationship is as defined according to Macromolecules, Vol. 9, pages 199-211 (1976), and is regarded as well known to a person skilled in the art. For greater clarity, we remind the reader below of this relationship, which connects the critical ratio of the reactive functional groups for two reactive components A and B (respectively a) and b) in our case) at the critical gel point $r_c$=(reactive functional groups of A)/(reactive functional groups of B) with the following relationship linking up the mean functionality $f_A$ of A, the mean functionality $f_B$ of B and the critical degree of conversion $x_g$ at the gelation point:

$$r_c * x_g^2 = 1/[(f_B-1)*(f_A-1)]$$

The objective is to adjust the ratio r=(reactive functional groups of A)/(reactive functional groups of B) so that it does not exceed a critical value for $x_g$ of approximately 1 (total conversion of the functional groups in deficit).

Subsequently, the same relationship should be observed for the reaction for the modification of the said intermediate compound c) with the said compound d) carrying an acrylate and p acrylates and/or methacrylates, the functionalities $f_A$ and $f_B$ being respectively replaced by those of c) and d). It is obvious that, in the case where just one acrylate group is present in the compound d), the risk of gelling does not exist by an amine-acrylate reaction because the methacrylate groups are not reactive by a Michael addition. Thus, the relationship should be considered in the case where at least two acrylates are present in d) and when the functionality of the polyamine a) is at least 3 in —NH—. It should be noted here that the functionality of c) in reactive —NH— groups is two for each residual reactive primary amine group and one for each residual reactive secondary amine group. Consequently, both the proportions and the functionalities of a) and b) in the first reaction stage for formation of m urethane-amines per molecule of the said compound c), like the proportions and functionalities of the said compound c) (residual reactive —NH— groups) and the said compound d) (acrylate) during the second reaction stage (formation of aminoacrylate by addition of —NH— to acrylate of d), observe, in each of the said two stages, the said relationship adapted (applied) to each of the said stages.

As regards its functionality in acrylates and/or methacrylates, the said oligomer according to the present invention can have a functionality f in acrylate or methacrylate groups which can vary from 1 to 30, with f=1 if monofunctional, preferably multifunctional oligomer with a functionality f ranging from 2 to 20, more particularly from 3 to 20.

More particularly, regarding p, which characterizes the number of acrylate and/or methacrylate functional groups carried per carbon-nitrogen (imine) bond formed by Michael addition, this parameter p can vary from 1 to 10; in particular, p=10 with polyacrylated oligomers, preferably from 1 to 5; in particular, p=5 with MFA monomers, such as dipentaerythritol, as compound d) as defined according to the invention.

In fact, the carbon-nitrogen (imine) bond formed by the said Michael addition in the second stage corresponds to an —N—CH$_2$—CH$_2$—CO$_2$—R$_5$(—O$_2$C—CH=CH—R$_6$)$_p$ group, with R$_6$ being H or methyl or H and methyl if p is different from 1, which group is an aminoacrylate carrying p acrylate and/or methacrylate groups.

According to a more preferred specific case, the said oligomer according to the invention corresponds to m=2 and p=2 to 10, preferably p=3 to 5.

According to a particular option of the said oligomer according to the invention, the number of residual reactive amine —NH— groups of the said intermediate product c) is equal to the number of moles of the said compound d).

According to another particular option of the said oligomer according to the invention, the said compound d) is in molar excess with respect to the residual reactive amine —NH— groups of the said intermediate product c) and thus the said residual compound d) is present in the said oligomer as reactive diluent.

The molar excess of d) means that there is more than one mole of compound d) per residual reactive amine —NH— group of the said product c). The content of residual compound d) corresponds to this molar excess (difference in moles of d)) with respect to the said reactive amine —NH— groups, which excess by definition could not react with c).

According to an alternative definition of the oligomer of the invention with respect to its structure, it is a urethane oligomer of linear or branched structure carrying one or more acrylate and/or methacrylate groups, in particular carrying at least two acrylate and/or methacrylate groups and more particularly carrying more than two acrylate and/or methacrylate groups, the said oligomer being characterized in that it comprises at least one oligomer with a structure according to the following general formula (III):

(Acr)$_p$-R$_5$—O$_2$C—CH$_2$—CH$_2$—(R$_7$)N-A-U—R$_3$[—U-A-[—N(R$_7$)—CH$_2$—CH$_2$—CO$_2$—R$_5$-(Acr)$_p$]$_{n-1}$]$_{m-1}$, with
Acr: acrylate or methacrylate group,
R$_5$: residue of a compound d) carrying an acrylate group and p additional acrylate and/or methacrylate groups, with p being equal to at least 1, in particular with d) and R$_5$ being defined as described above according to the invention,
A: residual of polyamine as defined according to a) as described above according to the invention, carrying n secondary or primary amine groups, with n ranging from 2 to 5,
R$_3$: residual of carbonate b) carrying m cyclic carbonate groups having 5 or 6 atoms, with m ranging from 1 to 2, the said residual optionally being hydroxylated and/or the said carbon ring optionally being substituted, in particular with b) and R$_3$ being defined as described above according to the invention,
R$_7$: cycloalkyl or C$_1$-C$_3$ alkyl, if secondary amine or R$_7$: —CH$_2$—CH$_2$—CO$_2$—R$_5$-(Acr)$_p$, if primary amine,
Acr: acrylate or methacrylate or acrylate+methacrylate mixture,
U: urethane bond formed by reaction of cyclic carbonate with secondary amine (—NH—) or primary amine (—NH$_2$), with an OH in the beta or gamma position as a function of the number of atoms of the carbonate ring respectively having 5 or 6 atoms.

The second subject-matter of the invention relates to a process for the preparation of the said oligomer as defined above according to the present invention, which process comprises the following stages:

i) reaction between the said polyamine a) and the said carbonate compound b) carrying m cyclic carbonates, with a) and b) being as defined according to the invention, the said polyamine being in stochiometric excess with respect to b) and being gradually added to the said carbonate b) present at the start in the reactor and the said reaction giving an intermediate product c) carrying m urethane groups and m hydroxyl groups in the alpha or beta position with respect to the said urethane and carrying the residual amine —NH— groups, ii) reaction for the modification of the said compound c), by addition of each of the said residual reactive amine groups of the said product c) to an acrylate group of a compound d) carrying, in addition to the said acrylate group, p additional acrylate and/or methacrylate groups, with each residual reactive amine —NH— group of the said product c) being thus converted into a carbon-nitrogen bond carrying the said acrylate and/or methacrylate groups, and thus production of the said urethane oligomer, with
the said polyamine a) carrying n primary and/or secondary amine groups and optionally at least one tertiary amine group, with n ranging from 2 to 5, preferably from 2 to 4 and more preferably from 2 to 3, more preferably still of 2,
the said carbonate b) carrying m carbonate groups with m ranging from 1 to 2, the ring of the said cyclic carbonate groups preferably being a ring having 5 or 6 atoms,
the said intermediate product c) carrying m urethane groups and m hydroxyl groups in the alpha or beta position with respect to the said urethane and from m*(n−1) to m*(2n−2) residual reactive amine —NH— groups,
the said compound d) carrying p acrylate and/or methacrylate groups in addition to the said acrylate group which reacts with one of the said residual reactive amine —NH— groups, with p being at least equal to 1 and preferably at least equal to 2, and
the number of the said residual reactive amine —NH— groups being less than or equal to the number of moles of the said compound d),
each carbon-nitrogen bond formed carrying p acrylate and/or methacrylate groups and the said urethane oligomer having a functionality of acrylates and/or methacrylates ranging from m*p(n−1) to m*p(2n−2).

More particularly, the reaction of stage i) can be carried out at a temperature ranging from 20 to 80° C., preferably from 45 to 65° C., and the reaction of stage ii) can be carried out at a temperature ranging from 80 to 95° C., preferably from 80 to 90° C.

The present invention also relates to the said intermediate product c) which is a hydroxylated polyurethane-amine as defined above as product of the first reaction stage i) as described in the definition of the urethane oligomer product of the invention or of the process for the preparation of the said oligomer according to the present invention.

More particularly, the said product is the intermediate product c) of the reaction i) between the said polyamine a)

as defined above and the said carbonate b) as defined above or the same product c) as obtained at the end of stage i) of the process for the preparation of the said oligomer according to the invention.

Another subject-matter of the invention is a crosslinkable composition, which composition comprises, as binder, at least one oligomer as defined above or as obtained by a process as defined above according to the invention. More particularly, the said composition can be crosslinked by the radiation route and/or by the thermal or low-temperature peroxide route and/or by the Michael-type addition route, in particular in the case of oligomers carrying at least two acrylate functional groups, and/or by another dual route which can involve at least two of the abovementioned routes and/or all of a portion of the m residual hydroxyl groups of the said oligomer by reaction of these residual hydroxyl groups with a crosslinking agent which reacts with the said hydroxyls. The said hydroxyls are secondary and in the beta or gamma position with respect to the urethane bond formed by reaction between cyclic carbonate functional group and beta or gamma amine functional group, depending on the number (respectively 5 or 6) of atoms of the carbonate ring of b). In particular, the secondary hydroxyl is in the beta position (ring having 5 atoms for b)). Mention may be made, as such suitable agents, of dianhydrides or melamine, in particular dianhydrides.

With respect to its potential use, the said crosslinkable composition of the invention can be a coating composition, preferably coatings from paints, varnishes and inks, a moulding composition, a leaktightness agent or chemical sealing composition, an adhesive composition, a composition for systems for the layer-by-layer manufacture of 3D objects, a composition for 3D printing systems, a concrete composition or a composite composition.

Another subject-matter of the invention is the use of an oligomer as defined above according to the invention or obtained by the process of the invention described above, the said oligomer being used as reactive binder in coating compositions, in this case including paints, varnishes and inks, adhesive compositions, moulding compositions, leaktightness agent compositions, chemical sealing compositions, compositions for systems for the layer-by-layer manufacture of 3D objects, compositions for 3D printing systems, concrete compositions or composite compositions.

Finally, the present invention also covers the finished product which results from the use of at least one oligomer as defined according to the invention or obtained by the process of the invention described above, which product is preferably chosen from coatings, in particular paints, varnishes and inks, or from adhesive seals, moulded parts, 3D objects obtained layer-by-layer, 3D printings, leaktight seals, chemical sealing, finished concrete or composite articles.

EXAMPLES

The examples which follow are given by way of illustration of the invention and of its performance and do not in any way limit its coverage.

EXPERIMENTAL PART

1) Preparation of Oligomers According to the Invention

Example 1

161.55 g of propylene carbonate (Huntsman Jeffsol, Mw of 102 g/mol), 0.81 g of tris(nonylphenyl) phosphite and 1 g of 2,6-di(tert-butyl)-4-methylphenol (BHT) are introduced into a 1 l reactor. 146.80 g of N-methyl-1,3-propanediamine (Aldrich, Mw of 88.15 g/mol) are added over one hour at a constant flow rate with stirring and bubbling with nitrogen. An exothermicity of approximately 30° C. is observed. At the end of the addition, the temperature of the mixture is brought to 60° C. After one hour at 60° C., while bubbling with air, 689.85 g of tripropylene glycol diacrylate (TPGDA, Sartomer SR306, Mw of 300 g/mol) are added to the mixture in fifteen minutes at a constant flow rate. At the end of the addition, the temperature of the mixture is brought to 85-90° C.

The progress of the reaction is monitored by a measurement of the total amine and tertiary amine numbers. The reaction is halted when the tertiary amine number=total amine number.

Example 2

162.93 g of propylene carbonate (Huntsman Jeffsol, Mw of 102 g/mol), 0.81 g of tris(nonylphenyl) phosphite and 1 g of 2,6-di(tert-butyl)-4-methylphenol (BHT) are introduced into a 1 l reactor. 147.81 g of N-methyl-1,3-propanediamine (Aldrich, Mw of 88.15 g/mol) are added over one hour at a constant flow rate with stirring and bubbling with nitrogen. An exothermicity of approximately 30° C. is observed. At the end of the addition, the temperature of the mixture is brought to 60° C. After one hour at 60° C., while bubbling with air, 687.44 g of trimethylolpropane triacrylate (TMPTA, Sartomer SR351, Mw of 296 g/mol) are added to the mixture in fifteen minutes at a constant flow rate. At the end of the addition, the temperature of the mixture is brought to 85-90° C.

The progress of the reaction is monitored by a measurement of the total amine and tertiary amine numbers. The reaction is halted when the tertiary amine number=total amine number.

Example 3

336.04 g of polyethylene oxide dicarbonate (Specific Polymers, Mw of 632.5 g/mol), 1.68 g of tris(nonylphenyl) phosphite and 2.07 g of 2,6-di(tert-butyl)-4-methylphenol (BHT) are introduced into a 1 l reactor. 95.38 g of N-methyl-1,3-propanediamine (Aldrich, Mw of 88.15 g/mol) are added over one hour at a constant flow rate with stirring and bubbling with nitrogen. An exothermicity of approximately 30° C. is observed. At the end of the addition, the temperature of the mixture is brought to 60° C. After one hour at 60° C., while bubbling with air, 564.84 g of trimethylolpropane triacrylate (TMPTA, Sartomer SR351, Mw of 296 g/mol) are added to the mixture in fifteen minutes at a constant flow rate. At the end of the addition, the temperature of the mixture is brought to 85-90° C.

The progress of the reaction is monitored by a measurement of the total amine and tertiary amine numbers. The reaction is halted when the tertiary amine number=total amine number.

2) Characteristics of the Products Prepared

| Characteristics | Unit | Example 1 | Example 2 | Example 3 |
| --- | --- | --- | --- | --- |
| Noury viscosity | Pa · s | 2.0 (25° C.) | 24 (50° C.) | 12.3 (50° C.) |
| Rate of crosslinking under UV lamp | m/min | <10 | 50 | >80 |

-continued

| Characteristics | Unit | Example 1 | Example 2 | Example 3 |
|---|---|---|---|---|
| Persoz hardness | Number of oscillations | 60 | 75 | 103 |
| Flexibility | mm | N/DA | 20 | |
| Resistance to acetone | s | 10 | >300 | >300 |

The applicative properties are measured on a film crosslinked under a 120 W/cm "fusion" UV lamp starting from a mixture of urethane amino-acrylate according to the invention and Darocur® 1173 photoinitiator in the proportions of 96/4 w/w.

Methods Used

Determination of the Reactivity (Crosslinking Rate):

The mixture is applied as a 12 μm film to a contrast chart (Penoparc charts form 1B, Leneta) and is then crosslinked using a 120 W/cm Hg fusion lamp. The minimum rate of passage (in m/min) necessary in order to obtain a film dry to the touch is measured.

For the following tests of hardness, flexibility and resistance to acetone, the photocrosslinked films are left in a climate-controlled room (T=23° C.) for 24 hours after crosslinking and before the measurements.

Determination of the Persoz Hardness:

The mixture is applied as a 100 μm film to a sheet of glass and crosslinked by a 120 W/cm Hg fusion lamp at a rate of 8 m/min. The number of oscillations, before the oscillations die out (change from 12° to 40 in amplitude), of a pendulum in contact with the coated sheet of glass is measured according to Standard ISO 1522.

Determination of the Flexibility:

The mixture is applied as a 100 μm film to a smooth sheet of 25/100 mm in thickness (D-46 Q-Panel) and is then crosslinked by a 120 W/cm Hg fusion lamp at a rate of 8 m/min. The coated sheet is curved over cylindrical mandrels according to Standard ISO 1519. The result is expressed by the value (in mm) of the lowest radius of curvature which can be inflicted on the coating without it cracking or detaching from the support.

Determination of the Resistance to Acetone:

The mixture is applied as a 12 μm film to a sheet of glass and then crosslinked by a 120 W/cm Hg fusion lamp at a rate of 8 m/min. The coating is rubbed with a rag impregnated with acetone. The result is the time (expressed in seconds) beyond which the film detaches and/or disintegrates.

The invention claimed is:

1. A urethane oligomer which is monofunctional or multifunctional in acrylates and/or methacrylates, which can be obtained from the reaction of a specific polyamine a) with a cyclic carbonate compound b) carrying m cyclic carbonate groups, the polyamine being in stoichiometric excess with respect to b) and the reaction giving an intermediate product c) carrying m formed urethane groups, which groups carry residual reactive amine —NH— groups, and subsequently by an addition reaction of each of the residual reactive amine groups of the product c) with an acrylate group of a compound d) carrying, in addition to the acrylate group, p additional acrylate and/or methacrylate groups, with each residual reactive amine —NH— group of the product c) being thus converted into a carbon-nitrogen bond carrying the acrylate and/or methacrylate groups, and thus production of the urethane oligomer, with:

the polyamine a) being a secondary-primary diamine having a single primary amine group and a single secondary amine group according to formula a1):

$$R_1\text{—NH—}R_2\text{—NH—R}, \quad \text{a1)}$$

with R being H, $R_1$ being alkyl, the alkyl optionally being alkoxylated and a cycloalkyl, and $R_2$ selected from the group consisting of alkylene and cycloalkylene comprising an aliphatic C6 ring or aralkylene of valency n ranging from 2 to 5, with it being possible for $R_2$ to carry or comprise at least one tertiary amine group, the carbonate b) carrying m cyclic carbonate groups with m ranging from 1 to 2, the ring of the cyclic carbonate groups being a ring having 5 atoms, wherein carbonate b) is i) a complete or partial ester of a monomeric or oligomeric polyacid; ii) a complete or partial ether of a monomeric or oligomeric polyol with a hydroxylated carbonate; iii) a complete or partial ether of a phenolic derivative with a hydroxylated carbonate; iv) an ether of allyl or vinyl alcohol with a hydroxylated carbonate or a methacrylate of a hydroxylated carbonate; v) a carbonate obtained by addition of $CO_2$ to a precursor monomeric or oligomeric epoxidized compound; or vi) is the product of the reaction of dimethyl carbonate with an aliphatic or cycloaliphatic polyol with a functionality of from 2 to 6, the intermediate product c) carrying m urethane groups and m OH groups in the alpha or beta position with respect to the urethane group and c) carrying from $m*(n-1)$ to $m*(2n-2)$ residual reactive amine —NH— groups, wherein n equals 2, the compound d) carrying p acrylate and/or methacrylate groups in addition to the acrylate group which reacts with one of the residual reactive amine —NH— groups, with p being from 1 to 11, and the number of the residual reactive amine —NH— groups of the product c) being less than or equal to the number of moles of the compound d), each carbon-nitrogen bond formed carrying p acrylate and/or methacrylate groups and the urethane oligomer carrying m urethane groups and m hydroxyl groups in the alpha or beta position with respect to the urethane and having a functionality in acrylates and/or methacrylates ranging from $m*p(n-1)$ to $m*p(2n-2)$ wherein n equals 2, wherein the urethane oligomer has a general formula (I):

$$[RCH_2=C(R_6)\text{—}CO_2)_p\text{—}R_5\text{—}O_2C\text{—}CH_2\text{—}CH_2\text{—}N(R_1)\text{—}R_2\text{—}NH\text{—}CO_2\text{—}C(R_4)_2\text{—}CH(OH)\text{—}]_m R_3 \quad (I)$$

with

R1 being alkyl, the alkyl optionally being alkoxylated and a cycloalkyl, and

R2 selected from the group consisting of alkylene and cycloalkylene comprising an aliphatic C6 ring or aralkylene of valency n ranging from 2 to 5, with it being possible for R2 to carry or comprise at least one tertiary amine group, $R_3$ being a hydrocarbon radical of aliphatic, cycloaliphatic and aromatic structure and optionally hydroxylated or a simple hydrogen when m=1, $R_4$ selected from the group consisting of H and an optionally hydroxylated hydrocarbon substituent of aliphatic, cycloaliphatic or aromatic structure identical to or different from that of $R_3$ and it optionally being possible for R₄ to form a ring attached to the carbonate ring by two common carbon atoms, R₅ selected from the group consisting of: (i) a polyol residue chosen from optionally alkoxylated and/or substituted alkylene polyol, optionally substituted cycloalkylene polyol or aralkylene polyol optionally alkoxylated and/or substituted on the aromatic ring or polyether polyol or polyester polyol and (ii) a residue of a multifunctional epoxy acrylate compound carrying an acrylate group and p additional acrylate and/or methacrylate groups, R₆ selected from the group consisting of H or methyl or H and methyl if p is other than 1.

2. The oligomer of claim 1 wherein the compound d) has a formula of $R_5$—$(O_2CCH=CH_2)(-O_2CC(R_6)=CH_2)_p$ with $R_5$ being a hydrocarbon residue of valency p+1.

3. The oligomer of claim 1, wherein the secondary-primary diamine is selected from the group consisting of N-methyl-1,3-propanediamine, N-methylethane diamine, N-methyl-1,4-butanediamine and N-methyl-1,5-pentanediamine.

4. The oligomer of claim 1, wherein the compound d) is a multifunctional acrylic monomer having a functionality of at least 2 and ranging up to p+1 equal to 6 and selected from the group consisting of:
  d1) acrylate esters of alkoxylated or nonalkoxylated polyols, with polyols chosen from the group: trimethylolpropane, ditrimethylolpropane, pentaerythritol, dipentaerythritol, diethylene glycol, dipropylene glycol, tripropylene glycol, glycerol, propylene glycol, butanediol and hexanediol,
  d2) epoxy acrylates, and
  d3) aminoacrylates.

5. The oligomer of claim 1, wherein the compound d) is a multifunctional acrylic oligomer having a functionality of at least 2 and ranging up to p+1 equal to 12 and selected from:
  d4) acrylated acrylic oligomer which is an acrylated glycidyl methacrylate copolymer or acrylated styrene oligomer which is a copolymer of styrene with maleic anhydride or acrylic acid which is acrylated by hydroxyethyl acrylate,
  d5) acrylated hydroxylated oligomer, from acrylated hydroxylated polydienes,
  d6) acrylated epoxidized oil,
  d7) acrylated epoxidized oligodiene,
  d8) oligoether acrylates,
  d9) oligoester acrylates,
  d10) oligoaminoacrylates.

6. The oligomer of claim 1, wherein the functionality in acrylate and/or methacrylate groups varies from 1 to 30.

7. The oligomer of claim 1, wherein m=2 and p varies from 2 to 11.

8. The oligomer of claim 1, wherein the compound d) is in molar excess with respect to the amine —NH— groups of the intermediate product c) and with the residual compound d) being present in the oligomer as reactive diluent.

9. A crosslinkable composition comprising, as binder, at least one oligomer according to claim 1.

10. The crosslinkable composition of claim 9, wherein the crosslinkable composition can be crosslinked by the radiation route and/or by the thermal or low-temperature peroxide route and/or by the Michael-type addition route, in the case of oligomers carrying at least two acrylate functional groups, and/or by another dual route involving at least two of the routes mentioned and/or involving all or a portion of the m residual hydroxyl groups of the oligomer, by reaction of these residual hydroxyl groups with a crosslinking agent which reacts with the hydroxyls.

11. The crosslinkable composition of claim 9, wherein the crosslinkable composition is a coating composition, chosen from paints, varnishes and inks or a moulding composition, a leaktightness agent or chemical sealing composition, an adhesive composition, a composition for systems for the layer-by-layer manufacture of 3D objects, a composition for 3D printing systems, a concrete composition or a composite composition.

12. A urethane oligomer which is monofunctional or multifunctional in acrylates, which can be obtained from the reaction of a specific polyamine a) with a cyclic carbonate compound b) carrying m cyclic carbonate groups, the polyamine being in stoichiometric excess with respect to b) and the reaction giving an intermediate product c) carrying m formed urethane groups, which groups carry residual reactive amine —NH— groups, and subsequently by an addition reaction of each of the residual reactive amine groups of the product c) with a first acrylate group of a compound d) carrying, in addition to the first acrylate group, p additional acrylate groups, with each residual reactive amine —NH— group of the product c) being thus converted into a carbon-nitrogen bond carrying the acrylate groups, and thus production of the urethane oligomer,
with:
  the polyamine a) being a secondary-primary diamine having a single primary amine group and a single secondary amine group according to formula a1):

$R_1$—NH—$R_2$—NH—R,     a1)

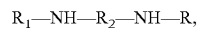

with R being H, $R_1$ being alkyl, the alkyl optionally being alkoxylated or a cycloalkyl, and $R_2$ being alkylene or cycloalkylene comprising an aliphatic C6 ring or aralkylene of valency n ranging from 2 to 5, with it being possible for $R_2$ to carry or comprise at least one tertiary amine group,
  the carbonate b) carrying m cyclic carbonate groups with m ranging from 1 to 2, the ring of the cyclic carbonate groups being a ring having 5 atoms, wherein carbonate b) is i) a complete or partial ester of a monomeric or oligomeric polyacid; ii) a complete or partial ether of a monomeric or oligomeric polyol with a hydroxylated carbonate; iii) a complete or partial ether of a phenolic derivative with a hydroxylated carbonate; iv) an ether of allyl or vinyl alcohol with a hydroxylated carbonate or a methacrylate of a hydroxylated carbonate; v) a carbonate obtained by addition of $CO_2$ to a precursor monomeric or oligomeric epoxidized compound; or vi) is the product of the reaction of dimethyl carbonate with an aliphatic or cycloaliphatic polyol with a functionality of from 2 to 6,
  the intermediate product c) carrying m urethane groups and m OH groups in the alpha or beta position with respect to the urethane group and c) carrying from m*(n−1) to m*(2n−2) residual reactive amine —NH— groups, wherein n equals 2,
  the compound d) carrying p acrylate groups in addition to the first acrylate group which reacts with one of the residual reactive amine —NH— groups, with p being from 1 to 11, and
  the number of the residual reactive amine —NH— groups of the product c) being less than or equal to the number of moles of the compound d),
  each carbon-nitrogen bond formed carrying p acrylate groups and the urethane oligomer carrying m urethane groups and m hydroxyl groups in the alpha or beta position with respect to the urethane and having a functionality in acrylates ranging from m*p(n−1) to m*p(2n−2) wherein n equals 2, wherein the urethane oligomer has a general formula (I):

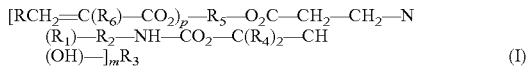

$[RCH_2\!=\!C(R_6)\!-\!CO_2)_p\!-\!R_5\!-\!O_2C\!-\!CH_2\!-\!CH_2\!-\!N(R_1)\!-\!R_2\!-\!NH\!-\!CO_2\!-\!C(R_4)_2\!-\!CH(OH)\!-\!]_m R_3$ (I)

with

R1 being alkyl, the alkyl optionally being alkoxylated and a cycloalkyl, and

R2 selected from the group consisting of alkylene and cycloalkylene comprising an aliphatic C6 ring or aralkylene of valency n ranging from 2 to 5, with it being possible for R2 to carry or comprise at least one tertiary amine group, $R_3$ being a hydrocarbon radical of aliphatic, cycloaliphatic or aromatic structure and optionally hydroxylated or a simple hydrogen when m=1, $R_4$ selected from the group consisting of H and an optionally hydroxylated hydrocarbon substituent of aliphatic, cycloaliphatic or aromatic structure identical to or different from that of $R_3$ and it optionally being possible for $R_4$ to form a ring attached to the carbonate ring by two common carbon atoms, $R_5$ selected from the group consisting of: (i) a polyol residue chosen from optionally alkoxylated and/or substituted alkylene polyol, optionally substituted cycloalkylene polyol or aralkylene polyol optionally alkoxylated and/or substituted on the aromatic ring or polyether polyol or polyester polyol and (ii) a residue of a multifunctional epoxy acrylate compound carrying an acrylate group and p additional acrylate groups, $R_6$ being H or methyl or H and methyl if p is other than 1.

* * * * *